(12) United States Patent
Jamar et al.

(10) Patent No.: US 6,583,796 B2
(45) Date of Patent: Jun. 24, 2003

(54) METHOD AND APPARATUS FOR DISPLAYING INFORMATION RETRIEVED FROM AN IMPLANTED MEDICAL DEVICE

(75) Inventors: Pamela Jamar, Plymouth, MN (US); James D. Webb, Maple Grove, MN (US); Paul Blowers, St. Paul, MN (US); Denise Dirnberger, Blaine, MN (US); Karen A. Stone, White Bear Lake, MN (US); Kevin T. Ousdigian, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 304 days.

(21) Appl. No.: 09/737,115

(22) Filed: Dec. 14, 2000

(65) Prior Publication Data

US 2002/0077561 A1 Jun. 20, 2002

(51) Int. Cl.⁷ .......................... G09G 5/00; A61B 5/044; A61N 1/372
(52) U.S. Cl. .......................... 345/804; 600/525; 607/32
(58) Field of Search ................................ 600/523, 525; 607/30, 32, 59, 60; 345/804–805, 781, 700, 961

(56) References Cited

U.S. PATENT DOCUMENTS

| | | | |
|---|---|---|---|
| 5,224,486 A | | 7/1993 | Lerman et al. |
| 5,284,152 A | | 2/1994 | Portnuff et al. |
| 5,483,468 A | | 1/1996 | Chen et al. |
| 5,491,781 A | | 2/1996 | Gasperina |
| 5,716,384 A | * | 2/1998 | Snell .......................... 607/30 |
| 5,833,623 A | * | 11/1998 | Mann et al. ................. 600/523 |
| 5,951,484 A | | 9/1999 | Hoium et al. |
| 5,956,013 A | | 9/1999 | Raj et al. |
| 6,014,581 A | | 1/2000 | Whayne et al. |
| 6,129,678 A | | 10/2000 | Ryan et al. |
| 6,154,668 A | | 11/2000 | Pedersen et al. |
| 6,161,039 A | * | 12/2000 | Krichen et al. ............. 600/523 |
| 6,289,244 B1 | * | 9/2001 | Conley et al. ................ 607/27 |
| 6,405,086 B1 | * | 6/2002 | Conley et al. ................ 607/27 |
| 6,473,638 B2 | * | 10/2002 | Ferek-Petric ................ 600/523 |

* cited by examiner

Primary Examiner—Sy D. Luu
(74) Attorney, Agent, or Firm—Girma Wolde-Michael (57) ABSTRACT

A graphical user interface is provided controllably displaying information retrieved from an implantable device, such as a pacemaker. The graphical user interface is comprised of a first and second window. The first window is adapted to display data identifying a plurality of episodes recorded by the implantable device, wherein the data is comprised of a plurality of fields. One of the fields may be used to identify a type of episode, such as ventricular tachycardia (VT), atrial and ventricular tachycardia (A&V), atrial fibrillation (AF), atrial flutter (Afl), atrial tachycardia (AT), and premature atrial contraction (PAC). The second window is adapted to display data types, such as VT, A&V, AF, Afl, AT, and PAC, that may be present in the plurality of fields, wherein at least one of the data types may be selected to filter the episodes displayed in the first window and display those episodes having the selected data types.

23 Claims, 11 Drawing Sheets

Collected Data - Arrhythmia Episodes

○ All Episodes 24-Feb-1997-04-Jul-1997
○ Only: ☐ VT ☐ AF ☐ A&V
       ☐ AT ☐ All ☐ PACs Sorted by: Type, Date Time ☐ > 0 sec
☐ ⊞

| Type | | Date/Time | | Duration hh mm ss | Max Rate AS/VS(bpm) | Activity At Onset | Strip? |
|---|---|---|---|---|---|---|---|
| VT | Last | 03-Jul-97 | 12:11 PM | :16 | 88/180 | Rest | ⊠⊠ |
| VT | Longest | 01-Jun-97 | 04:55 PM | :23 | 65/180 | Rest | |
| VT | | 01-Jun-97 | 04:55 PM | :17 | 70/230 | Rest | |
| VT | | 01-Jun-97 | 04:54 PM | :17 | 70/220 | Rest | ⊠ |
| VT | Fastest | 01-Jun-97 | 04:54 PM | :13 | 70/270 | Rest | |
| VT | | 01-Jun-97 | 11:07 PM | :15 | 70/220 | Rest | |
| VT | | 31-May-97 | 08:16 PM | :16 | 85/540 | Rest | |
| VT | | 31-May-97 | 05:41 PM | :17 | 80/250 | Rest | |
| VT | | 31-May-97 | 05:18 PM | :16 | 75/260 | Rest | |

[Open Detail]

• Mode Switched

A.EGM
V.EGM

METHOD AND APPARATUS FOR DISPLAYING INFORMATION RETRIEVED FROM AN IMPLANTED MEDICAL DEVICE

BACKGROUND OF THE INVENTION

1. Field of the Invention

This invention relates generally to a method and apparatus for displaying data, and, more particularly, to a method and apparatus for displaying data related to cardiac episodes, which have been recorded by an implanted medical device.

2. Description of the Related Art

Since the introduction of the first implantable pacemakers in the 1960s, there have been considerable advancements in both the field of electronics and medicine, such that there is presently a wide assortment of commercially available body-implantable electronic medical devices. The class of implantable medical devices now includes pacemakers, implantable cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well proven.

As the functional sophistication and complexity of implantable medical device systems have increased over the years, it has become increasingly useful to include a system for facilitating communication between one implanted device and another implanted or external device, for example, a programming console, monitoring system, or the like. Shortly after the introduction of the earliest pacemakers, it became apparent that it would be desirable for physicians to non-invasively obtain information regarding the operational status of the implanted device, and/or to exercise at least some control over the device, e.g., to turn the device on or off or adjust the pacing rate, after implant. As new, more advanced features have been incorporated into implantable devices, it has become increasingly useful to convey correspondingly more information to/from the device relating to the selection and control of those features.

Additionally, for diagnostic purposes, it is desirable for the implanted device to be able to communicate information regarding the device's operational status and the patient's condition to the physician or clinician. In fact, a wide variety of data may be collected by the implanted device and provided to the physician or clinician. The data provided by the implanted device may be real-time or recorded data. For example, implantable devices are available that can transmit a digitized electrical signal reflecting electrical cardiac activity (e.g., an ECG, EGM or the like) for display, storage, and/or analysis by an external device. In addition, known pacemaker systems have been provided with what is referred to as Marker Channel™ functionality, in which information regarding the pacemaker's operation and the occurrence of physiological events is communicated to an external programming unit. The Marker Channel™ information can then be printed or displayed in relation to an ECG so as to provide supplemental information regarding pacemaker operation. For example, events such as pacing or sensing of natural heartbeats are recorded with a mark indicating the time of the event relative to the ECG. This is helpful to the physician in interpreting the ECG, and in verifying proper operation of the pacemaker. One example of a Marker Channel™ system is disclosed in U.S. Pat. No. 4,374,382 to Markowitz, entitled "Marker Channel™ Telemetry System for a Medical Device." The Markowitz '382 patent is hereby incorporated by reference herein in its entirety.

The sheer volume of data and the varying forms in which it may be presented may reduce the effectiveness with which the physician and/or clinician may locate and analyze the data provided by the implanted device. That is, the physician and/or clinician may need to review a number of sets of data in an effort to locate those that show or otherwise illustrate the condition of the implanted device and/or patient in which he/she is interested. As the volume of data recorded and provided by the implanted device continues to increase, the difficulty of locating and analyzing relevant data may be exacerbated.

The present invention is directed to overcoming, or at least reducing the effects of, one or more of the problems set forth above.

SUMMARY OF THE INVENTION

In one aspect of the present invention, a method is provided for controllably displaying information retrieved from an implantable device. The method comprises displaying data in a first window identifying a plurality of episodes recorded by the implantable device, wherein the data is comprised of a plurality of fields. Data types that are present in the plurality of fields are displayed in a second window, wherein at least one of the data types may be selected to filter the episodes displayed in the first window and display those episodes having the selected data types.

In another aspect of the present invention, a graphical user interface is provided controllably displaying information retrieved from an implantable device. The graphical user interface is comprised of a first and second window. The first window is adapted to display data identifying a plurality of episodes recorded by the implantable device, wherein the data is comprised of a plurality of fields. The second window is adapted to display data types that may be present in the plurality of fields, wherein at least one of the data types may be selected to filter the episodes displayed in the first window and display those episodes having the selected data types.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
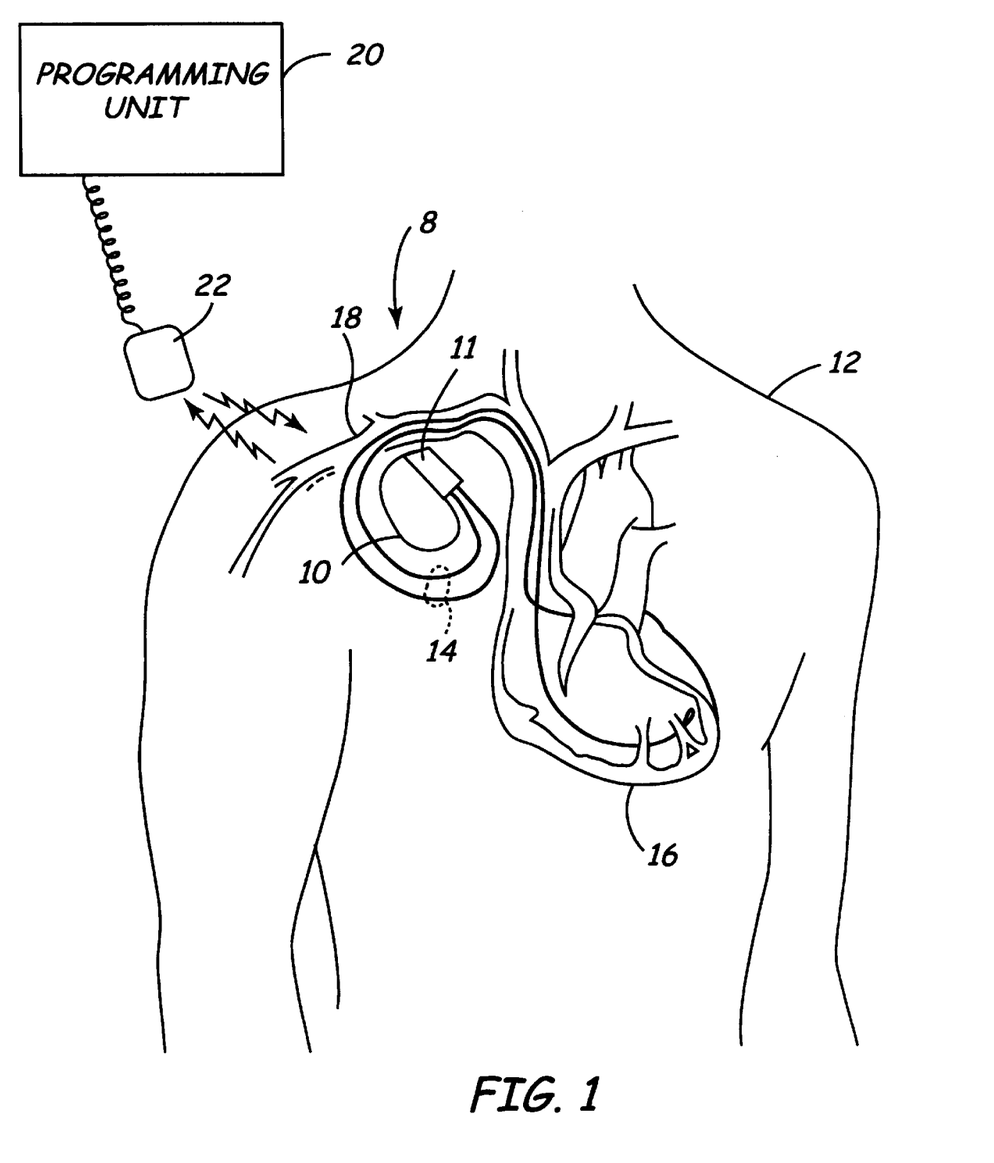
FIG. 1 schematically illustrates one embodiment of an implanted medical device in the form of a pacemaker and an associated external programming unit.

FIG. 1 illustrates an implantable medical device (IMD) system 8, which includes, for example, an implantable pacemaker 10 that has been implanted in a patient 12. The pacemaker 10 is housed within a hermetically sealed, biologically inert outer canister or housing, which may itself be conductive so as to serve as an electrode in the pacemaker's pacing/sensing circuit. One or more pacemaker leads, collectively identified with reference numeral 14 in FIG. 1 are electrically coupled to the pacemaker 10 in a conventional manner and extend into the patient's heart 16 via a vein 18. Disposed generally near a distal end of the leads 14 are one or more exposed conductive electrodes for receiving electrical cardiac signals or delivering electrical pacing stimuli to the heart 16. The leads 14 may be implanted with their distal end situated in either the atrium or ventricle of the heart 16.

Although the present invention is described herein in an embodiment that includes a pacemaker, it may be advantageously embodied in numerous other types of implantable medical device systems in which it is desirable to provide a communication link between two physically separated components and retrieve and display data stored therein.

FIG. 1 also depicts an external programming unit 20 for non-invasive communication with the implanted device 10 via conventional uplink and downlink communication channels, which are not described in greater detail herein so as to avoid unnecessarily obscuring the instant invention. Associated with the programming unit 20 is a programming head 22, in accordance with conventional medical device programming systems, for facilitating two-way communication between the pacemaker 10 and the programmer 20. In many known implantable device systems, the programming head 22, such as that depicted in FIG. 1, is positioned on the patient's body over the implant site of the device 10 (usually within 2- to 3-inches of skin contact), such that one or more antennas within the head 22 can send RF signals to, and receive RF signals from, an antenna (not shown) disposed within the hermetic enclosure of the implanted device 10 or disposed within a connector block 11 of the device 10, in accordance with common practice in the art.

Figure 2:
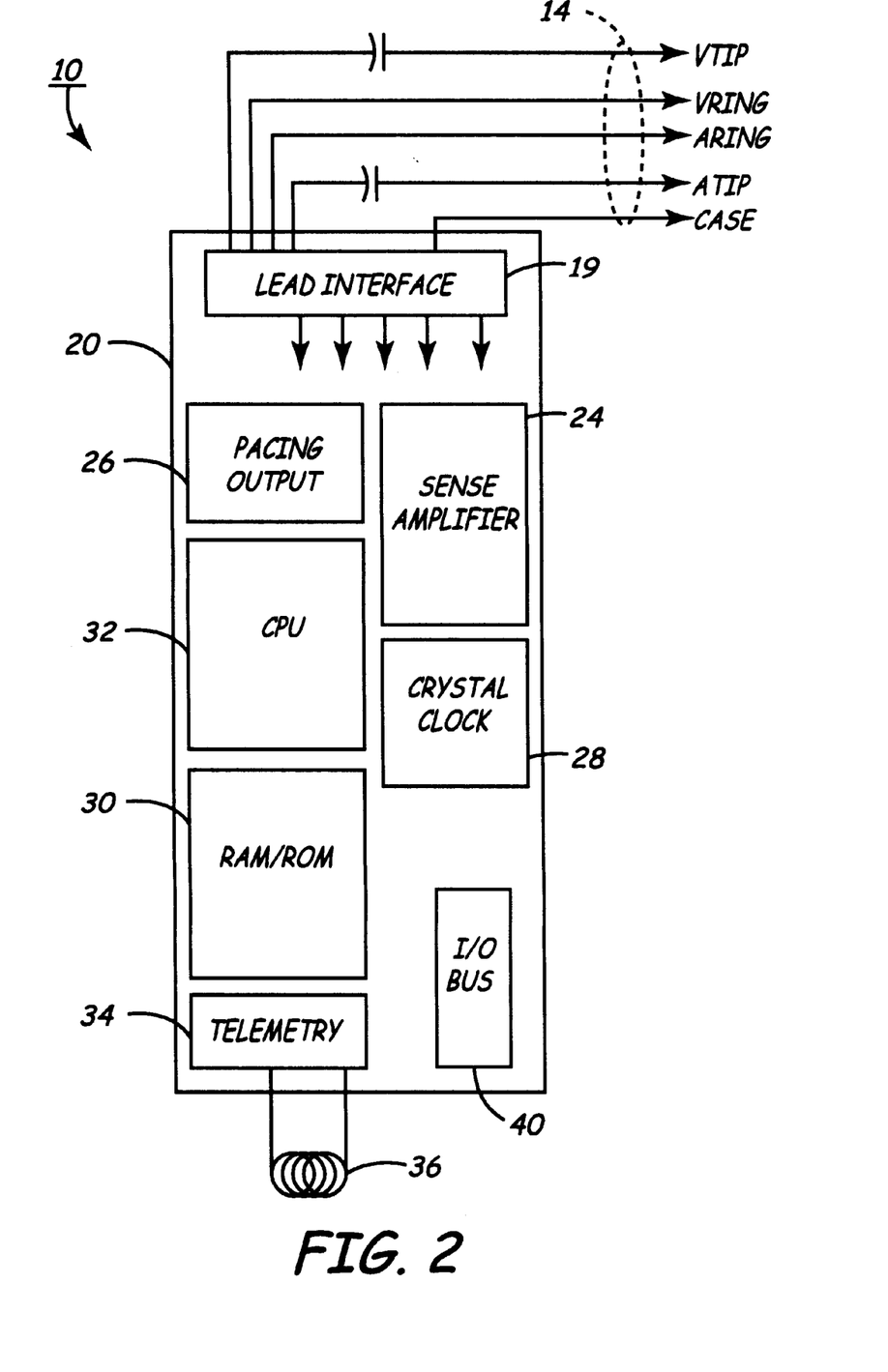
FIG. 2 schematically illustrates a high level block diagram of functional blocks of the implanted pacemaker of FIG. 1.

FIG. 2 provides a general block diagram of electronic circuitry that makes up the pacemaker 10. The pacemaker 10 is a conventional device capable of performing a variety of functions, such as delivering electrical stimulation therapy to the patient 12 in accordance with the presently disclosed embodiment of the invention. FIG. 2 shows that the pacemaker 10 comprises circuitry for controlling the device's pacing and sensing functions. The pacemaker circuitry may be of conventional design, in accordance, for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the pacemaker 10 are conventional in their design and operation, such components will not be described herein in detail, as it is believed that design and implementation of such components would be a matter of routine practice to those of ordinary skill in the art. For example, the circuitry of the pacemaker 10 shown in FIG. 2 includes sense amplifier circuitry 24, stimulating pulse output circuitry 26, a crystal clock 28, a random-access memory (RAM) and read-only memory (ROM) unit 30, and a pacing timing and control circuit in the form of a programmed central processing unit (CPU) 32, all of which are well-known in the art.

The pacemaker 10 also includes an internal telemetry communications circuit 34 coupled to an antenna 36 so that it is capable of communicating with the external programmer/control unit 20. Various telemetry systems for providing the uplink and downlink communication channels between the external programming unit 20 and the implanted pacemaker 10 have been shown in the art and may be employed herein without departing from the spirit and scope of the instant invention. Exemplary communication telemetry systems that may be utilized herein are disclosed, for example, in the following U.S. Patents: U.S. Pat. No. 4,539,992 to Calfee et al. entitled "Method and Apparatus for Communicating With Implanted Body Function Stimulator" "U.S. Pat. No. 4,550,732 to Batty Jr. et al. entitled "System and Process for Enabling a Predefined Function Within An Implanted Device;" U.S. Pat. No. 4,751,589 to Slocum et al. entitled "Biomedical Implant With High Speed, Low Power Two-Way Telemetry;" U.S. Pat. No. 4,676,248 to Berntson entitled "Circuit for Controlling a Receiver in an Implanted Device;" U.S. Pat. No. 5,127,404 to Wyborny et al. entitled "Telemetry Format for Implanted Medical Device;" U.S. Pat. No. 4,211,235 to Keller, Jr. et al. entitled "Programmer for Implanted Device;" the above-referenced Markowitz '382 patent; and U.S. Pat. No. 4,556,063 to Thompson et al. entitled "Telemetry System for a Medical Device." The Wyborny et al. '404 patent and the Thompson et al. '063 patent are hereby incorporated by reference herein in their respective entireties.

With continued reference to FIG. 2, the pacemaker 10 is coupled to one or more leads 14 that, when implanted, extend transvenously between the implant site of the pacemaker 10 and the patient's heart 16, as previously noted with reference to FIG. 1. Physically, the connections between the leads 14 and the various internal components of the pacemaker 10 are facilitated by a conventional connector block assembly 11, shown in FIG. 1 but not shown in FIG. 2. Electrically, the coupling of the leads 14 and the internal electrical components of the pacemaker 10 may be facilitated by a lead interface circuit 19, which functions, in a multiplexer-like manner, to selectively and dynamically establish necessary connections between various conductors in the leads 14, including, for example, atrial tip and ring electrode conductors ATIP and ARING and ventricular tip and ring electrode conductors VTIP and VRING, and individual electrical components of the pacemaker 10, as would be familiar to those of ordinary skill in the art. For the sake of clarity, the specific connections between the leads 14 and the various components of the pacemaker 10 are not shown in FIG. 2, although it will be clear to those of ordinary skill in the art that, for example, the leads 14 will necessarily be coupled, either directly or indirectly, to sense amplifier circuitry 24 and stimulating pulse output circuitry 26, in accordance with common practice, such that cardiac electrical signals may be conveyed to the sense amplifier circuitry 24, and such that stimulating pulses may be delivered to cardiac tissue, via the leads 14.

It will be appreciated that the signals received over the leads 14 by the sense amplifier circuitry 24 may be collected and stored in the RAM/ROM unit 30 by the CPU 32 acting under control of software also stored in the RAM/ROM unit 30. Additional data, such as the timing of signals delivered by the stimulating pulse output circuitry 26 may also be stored in the RAM/ROM unit 30. This stored data may be later retrieved and delivered to the programming unit 20 via the telemetry communications circuit 34. The pacemaker 10 may, in addition to its functions of monitoring cardiac activity and generating therapy pulses as required, detect the onset of various arrhythmia conditions in the heart and collect information related to those conditions. For example, the pacemaker 10 may detect the onset of a ventricular tachycardia (VT) event, and in response to that detection, the pacemaker 10 may collect certain data associated with that VT episode. The date and time of the episode may be noted and recorded. The duration of the episode and the maximum heart rate observed during the episode may also be noted and recorded. Also, EGM data and marker data associated with the episode may be recorded. One embodiment of the pacemaker 10, which may be used in conjunction with the instant invention, is disclosed in an application (docket P9226) filed Dec. 8, 2000, entitled "Prioritized Dynamic Memory Allocation of Arrhythmia Episode Detail Collection." Such application is hereby incorporated by reference herein in its entirety.

As previously noted, the circuitry of the pacemaker 10 includes the central processing unit (CPU) 32 which may be an off-the-shelf programmable microprocessor or microcontroller, but in the presently illustrated embodiment of the invention is a custom integrated circuit. Although specific connections between the CPU 32 and other components of the pacemaker circuitry are not shown in FIG. 2, it will be apparent to those of ordinary skill in the art that the CPU 32 functions to control the timed operation of the stimulating pulse output circuit 26 and the sense amplifier circuit 24 under control of a program of instructions stored in the RAM/ROM unit 30. The crystal clock 28 in the presently illustrated embodiment is a crystal controlled oscillator that provides a main timing clock signal. Again, the lines over which such clock signals are provided to the various components of the pacemaker 10 (e.g., the CPU 32) are omitted from FIG. 2 for the sake of clarity. It is believe that those of ordinary skill in the art will be familiar with such an operative arrangement.

It is to be understood that the various components of the pacemaker 10 depicted in FIG. 2 are powered by means of a battery (not shown), which is contained within the hermetic enclosure of the pacemaker 10, in accordance with common practice in the art. For the sake of clarity in the drawings, the battery and the connections between it and the other components of the pacemaker 10 are not shown.

Stimulating pulse output circuitry 26, which functions to generate cardiac stimuli under control of signals issued by the CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the present invention.

The sense amplifier circuitry 24, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety. Generally, the sense amplifier circuitry 24 functions to receive electrical cardiac signals from the leads 14 and to process such signals to derive event signals reflecting the occurrence of specific cardiac electrical events, including atrial contractions (P-waves) and ventricular contractions (R-waves). These event-indicating signals are provided to the CPU 32 for use by the CPU 32 in controlling the synchronous stimulating operations of the pacemaker 10 in accordance with common practice in the art. In addition, these event-indicating signals, as discussed above, may be communicated, via the uplink communication channel, to the external programming unit 20 for storage and visual display to a physician or clinician.

Those of ordinary skill in the art will appreciate that the pacemaker 10 may include numerous other components and subsystems, for example, activity sensors and associated circuitry. The presence or absence of such additional components in the pacemaker 10, however, is not believed to be pertinent to the present invention, which relates generally to the programming unit 20 and its method of operation.

Figure 3:
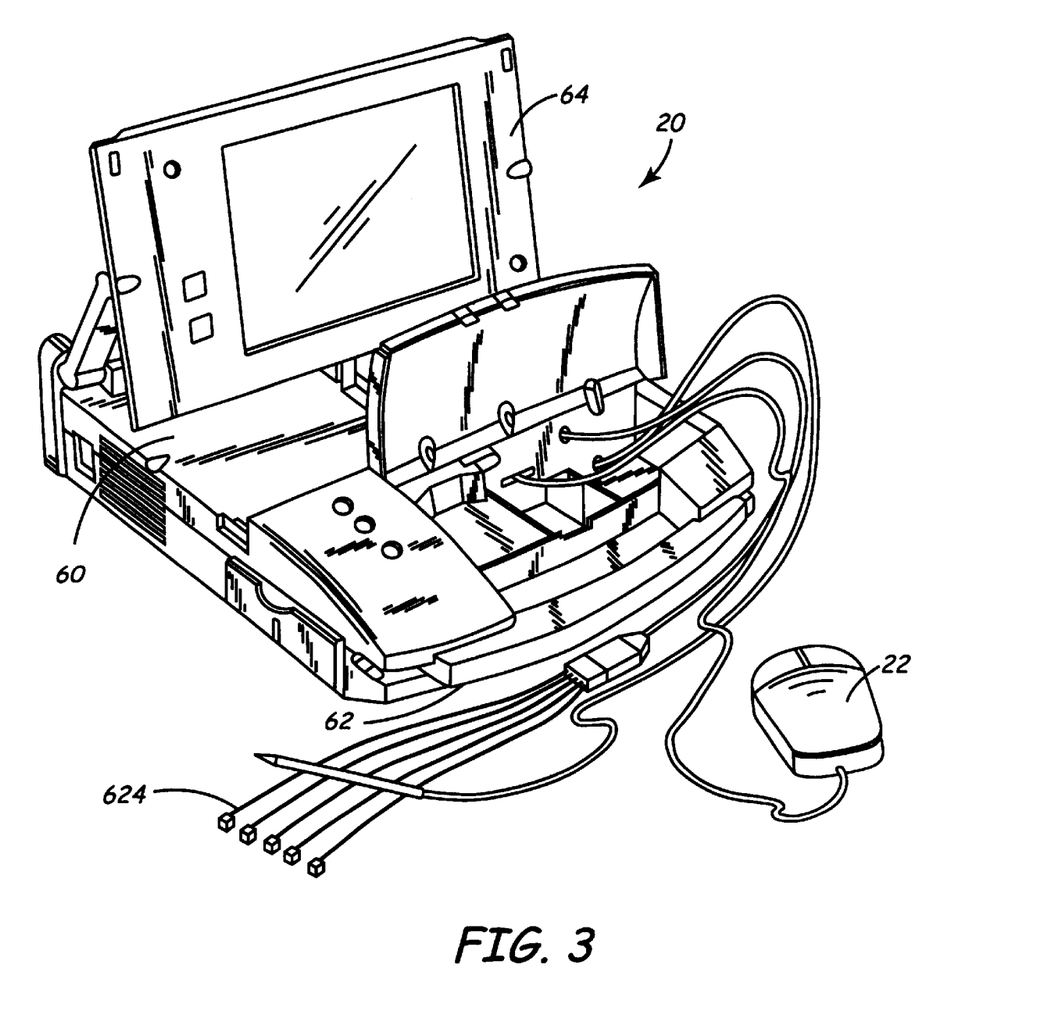
FIG. 3 illustrates an external perspective view of the external programming unit of FIG. 1.

FIG. 3 shows a perspective view of one embodiment of the programming unit 20 in accordance with the presently disclosed embodiment of the invention. The programming unit 20 comprises an outer housing 60, which is preferably made of thermal plastic or another suitably rugged yet relatively lightweight material. A carrying handle, designated generally as 62 in FIG. 3, is integrally formed into the front of the housing 60. With the handle 62, the programming unit 20 can be carried like a briefcase.

An articulating display screen 62 is disposed on an upper surface of the housing 60. The display screen 64 folds down into a closed position (not shown) when the programming unit 20 is not in use, thereby reducing the size of the programming unit 20 and protecting a display surface of the display 64 during transportation and storage thereof.

A floppy disk drive (not shown) is disposed within the housing 60 and is accessible via a disk insertion slot (not shown). A hard disk drive (not shown) is also disposed within the housing 60, and it is contemplated that a hard disk drive activity indicator (e.g., an LED, not shown) could be provided to give a visible indication of hard disk activation.

As would be appreciated by those of ordinary skill in the art, it is often desirable to provide a means for the programming unit 20 to adapt its mode of operation depending upon the type of implanted device with which it is to communicate. Accordingly, it may be desirable to have an expansion cartridge containing EPROMS or the like for storing program information to control the programming unit 20 to operate in a particular manner corresponding to a given type of implantable device. Alternatively, program information may be stored on the hard disk drive, on floppy diskettes that may be inserted in the floppy disk drive, or even on compact disks (CDs).

In accordance with the presently illustrated embodiment of the invention, the programming unit 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, the programming unit 20 is shown with the articulating display screen 64 having been lifted up into one of a plurality of possible open positions such that the display area thereof is visible to a user situated in front of the programming unit 20. The articulating display screen 64 is preferably of the LCD or electroluminescent type, characterized by being relatively thin as compared, for example, a cathode ray tube (CRT) or the like.

The display screen 64 is operatively coupled to computer circuitry disposed within the housing 60, and is adapted to provide a visual display of graphics and/or data under control of the internal computer.

One embodiment of the programming unit 20 described herein with reference to FIG. 3 is described in more detail in U.S. Pat. No. 5,345,362 issued to Thomas J. Winkler, entitled "Portable Computer Apparatus With Articulating Display Panel," which patent is hereby incorporated herein by reference in its entirety. Also, Medtone Model 9760 or 9790 programmers are other implantable device programming units with which the present invention may be advantageously practiced.

Figure 4:
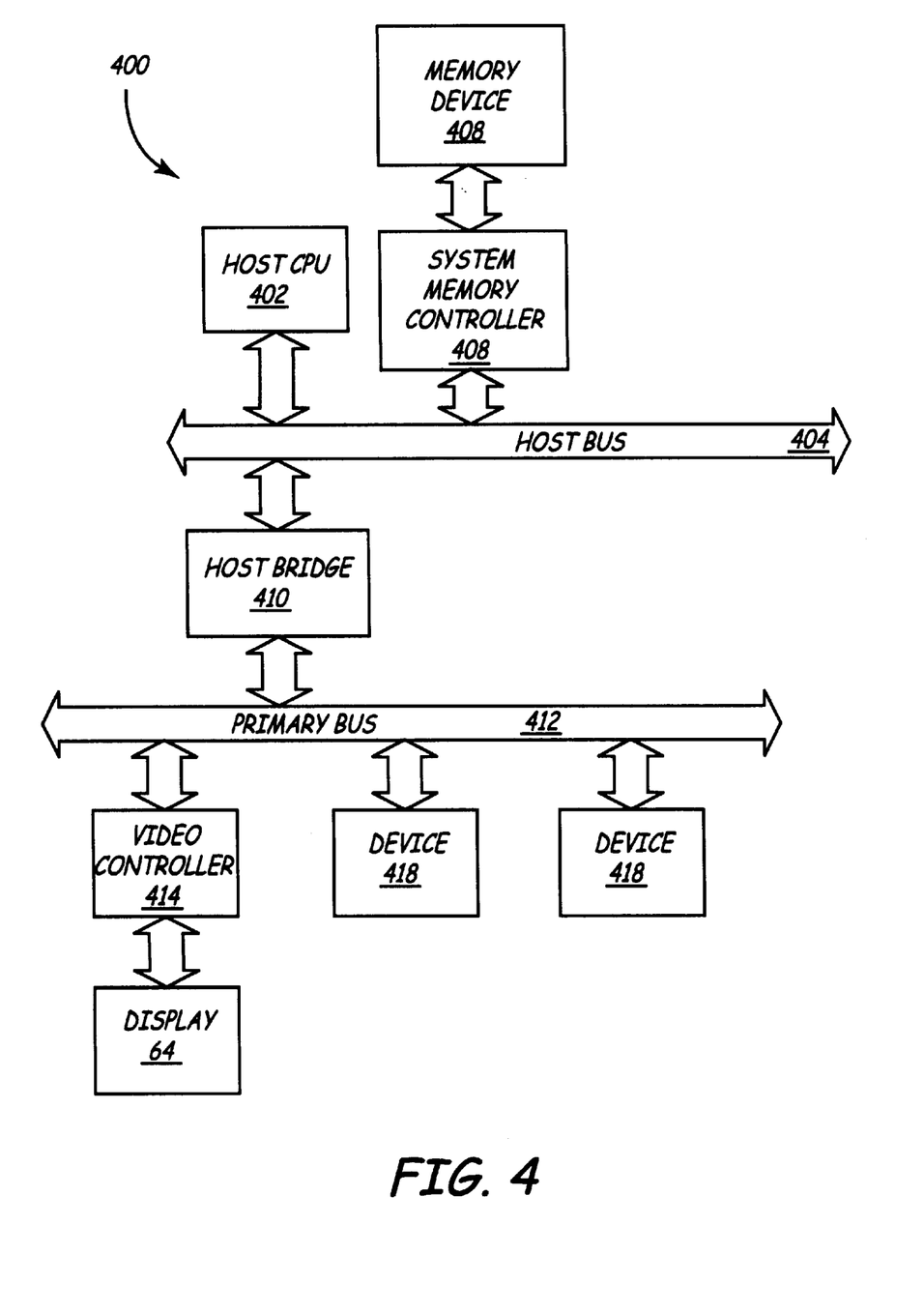
FIG. 4 illustrates one embodiment of an architectural configuration of the external programming unit of FIGS. 1 and 3.

Turning now to FIG. 4, a general block diagram of one embodiment of an architectural configuration of a conventional computer system 400 that may be used in the programming unit 20 is shown. The computer system 400 includes a processor 402, such as a microprocessor, which may include multiple processors (not shown), coupled to a host bus 404. A system memory controller 406 is coupled to the host bus 404 and a memory device 408. A host bridge 410 couples the host bus 404 to a primary bus 412, such as a peripheral component interconnect (PCI) bus (PCI Specification, Rev. 2.1). A video controller 414 and other devices 416 (e.g., PCI devices) are coupled to the primary bus 412. The computer system 400 may include other buses such as a secondary PCI bus (not shown) or other peripheral devices (not shown) known in the art.

The processor 402 communicates with the memory device 408 through the system memory controller 406. The system memory controller 406 is of a conventional construction, providing memory addresses and logic signals to the memory device 408 to characterize the desired memory transactions. The memory device 408 may take on any of a variety of forms, such as a synchronous dynamic random access memory (SDRAM), double-rate dynamic random access memory (DDRAM), or the like, without departing from the spirit and scope of the instant invention.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Figure 5:
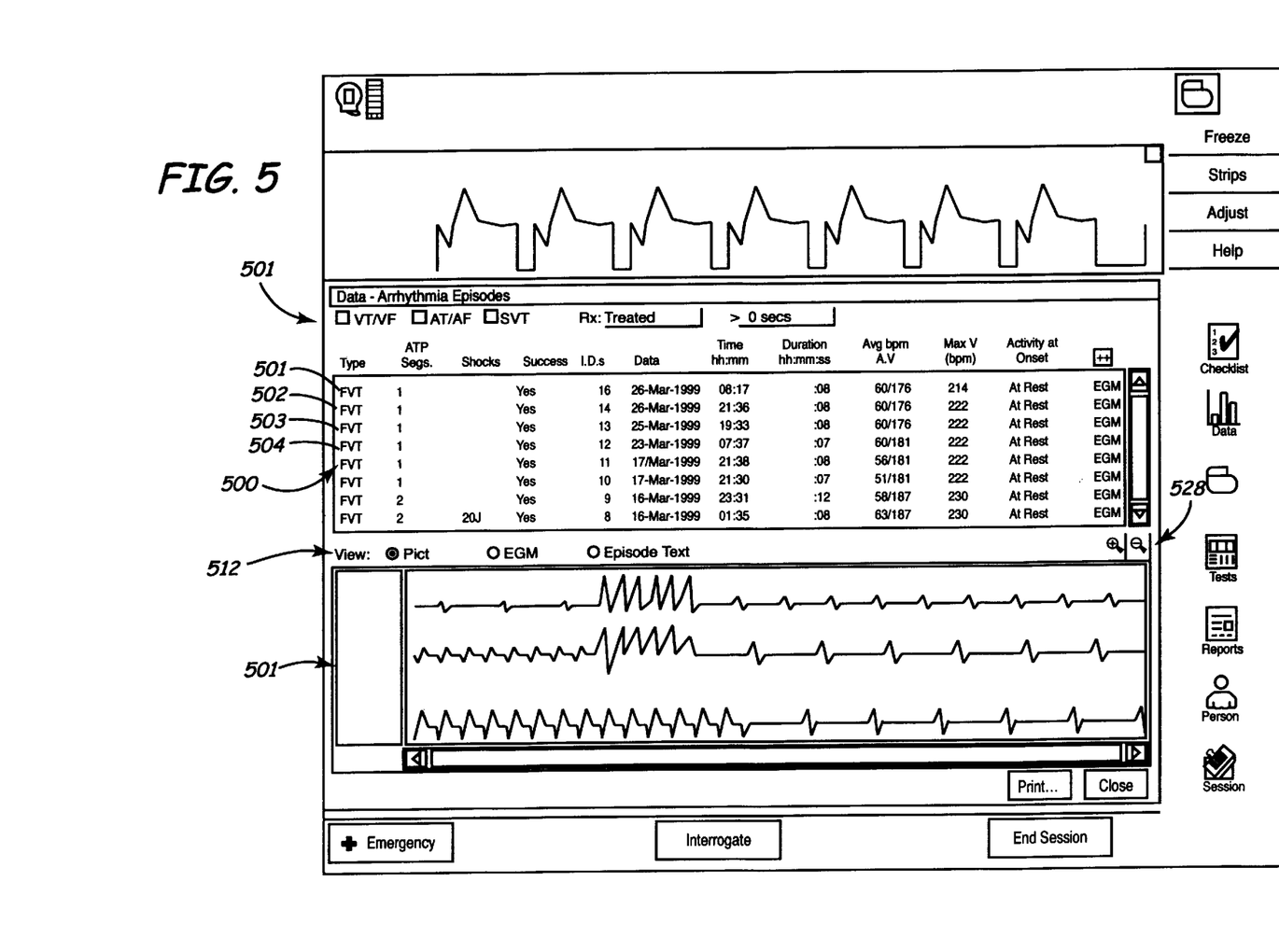
FIG. 5 illustrates one embodiment of a graphical user interface in a first operational state.

Generally, software, such as application programs and drivers, is stored in the memory device 408 and executed by the processor 402. Any of a variety of application programs may be stored in the memory device 408 and executed by the processor 402. For example, an application program may be used to retrieve and display data received from the pacemaker 10 in a format illustrated in FIG. 5. FIG. 5 shows the presentation of data as it is shown on the display 64 of the programming unit 20. That is, FIG. 5 represents the physician's/clinician's view of the display 64 during an actual session. In other words, FIG. 5 shows at least a portion of a graphical user interface (GUI) for the application program that may be used to display, filter, sort, and otherwise analyze data collected by the pacemaker 10.

Generally, the pacemaker 10 has recorded a series of cardiac episodes, such as ventricular tachycardia (VT), atrial and ventricular tachycardia (A&V), atrial fibrillation (AF), atrial flutter (Afl), atrial tachycardia (AT), and premature atrial contraction (PAC). Data associated with and identifying each of these events may be listed in a window 500 in the GUI. For example, in the embodiment illustrated in FIG. 5, a series of these events are displayed in the window 500, each on a separate line 501, 502, 503, 504. At least a portion of the data associated with each of these events may be set forth in the window 500 on their associated line 501, 502, 503, 504. For example, the line 501 indicates that the illustrated event includes data, such as the type of event, the date, the duration, whether an EGM was recorded, and the like.

Figure 6:
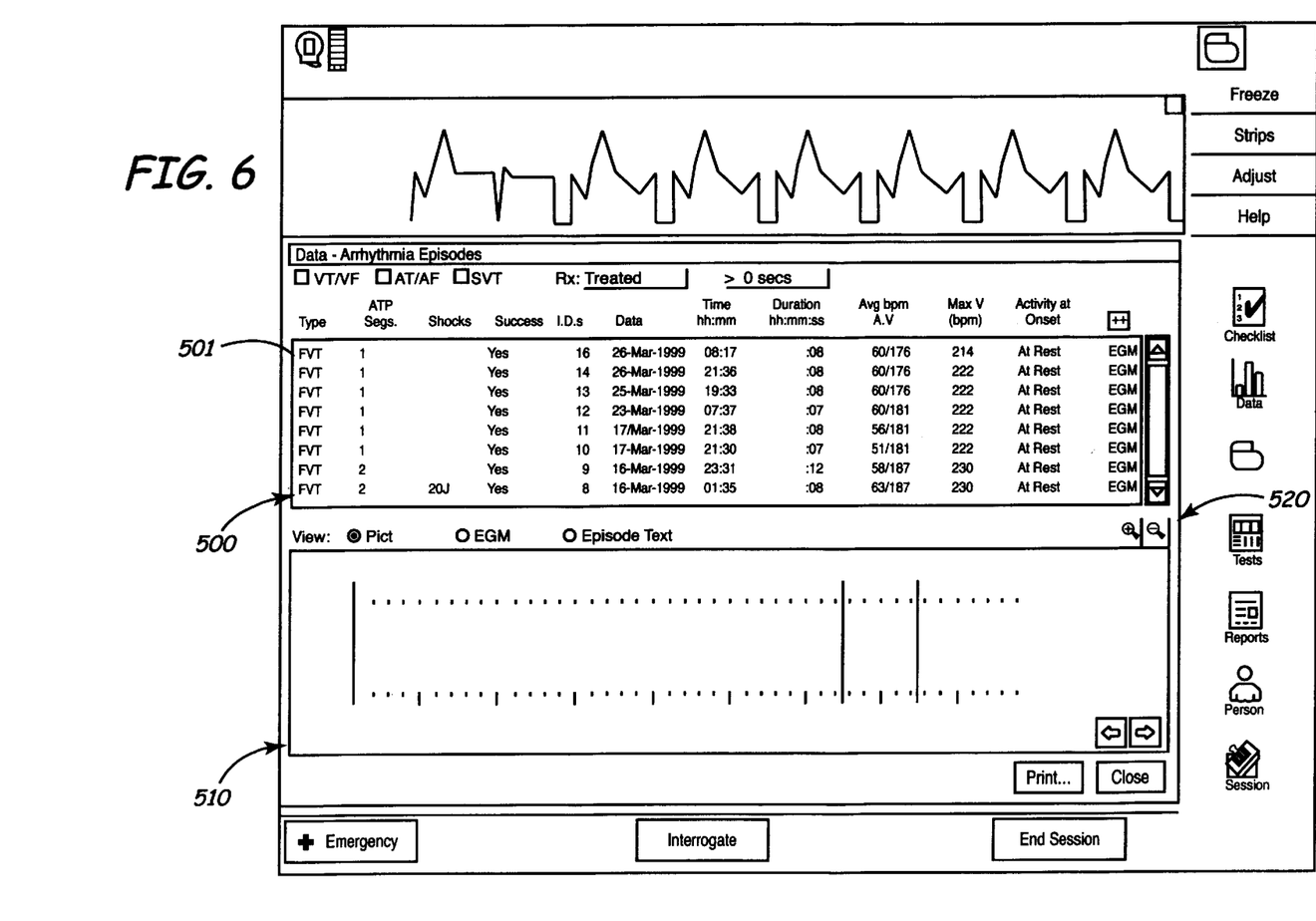
FIG. 6 illustrates one embodiment of a graphical user interface in a second operational state.

The physician/clinician may select one of the events, using the keyboard or other pointing device. For example, the line 502 has been selected in the embodiment illustrated in FIG. 5. Once the desired line has been selected, graphical representations of any data recorded by the pacemaker 10 during the event may be presented in a second window 510. For example, in the embodiment illustrated in FIG. 5, the EGM associated with the event identified in the line 502 has been displayed in the window 510. Other data may also be displayed in the window 510 by selecting the type of data desired to be displayed. Selecting the type of data may be accomplished by positioning the pointing device over an area of the GUI identified by the designation View 512. That is, in the illustrated embodiment, the physician/clinician may display a Plot, the EGM, or Episode Text in the Window 510 by selecting the appropriate item, such as by a radio button or check box in the GUI. FIG. 6, for example, illustrates a view of the GUI where the physician/clinician has elected to display in the window 510 a plot of data associated with the event shown in line 501. The line 501 is highlighted, indicating that it has been selected by the physician/clinician, and the radio button associated with the Plot feature of the View portion 512 of the GUI has been selected.

Of course, the selected data may only be displayed if it has been recorded by the pacemaker 10 and transferred to the programming unit 20. That is, an EGM may not be recorded for all events, depending on the programming of the pacemaker 10.

The events displayed in the window 500 may likewise be selected by the physician/clinician. That is, the GUI includes an area 514 in which the physician/clinician may select one or more types of events to be displayed in the window 500. While many events of varying type may be stored within the memory of the programming unit 20 (as discussed above), the physician/clinician may desire to see only certain types of events or episodes that are useful in diagnosing a particular condition of the patient, or of the pacemaker 10. The GUI may include radio buttons, check boxes, or the like for selecting events such as VT/VF, AT/AF, SVT, and the like. Once the selections are made, software contained in the programming unit 20 will filter or otherwise search through a database of events and select only those identified in the area 514 of the GUI. The physician/clinician may select one or more types of events to be filtered and displayed in the window 500. For example, in the exemplary embodiments illustrated in FIGS. 5 and 6, both the VT/VF and AT/AF types of events have been selected. Fewer or more events may be selected according to the present needs of the physician/clinician in diagnosing the condition of the patient and/or pacemaker 10.

Figure 7:
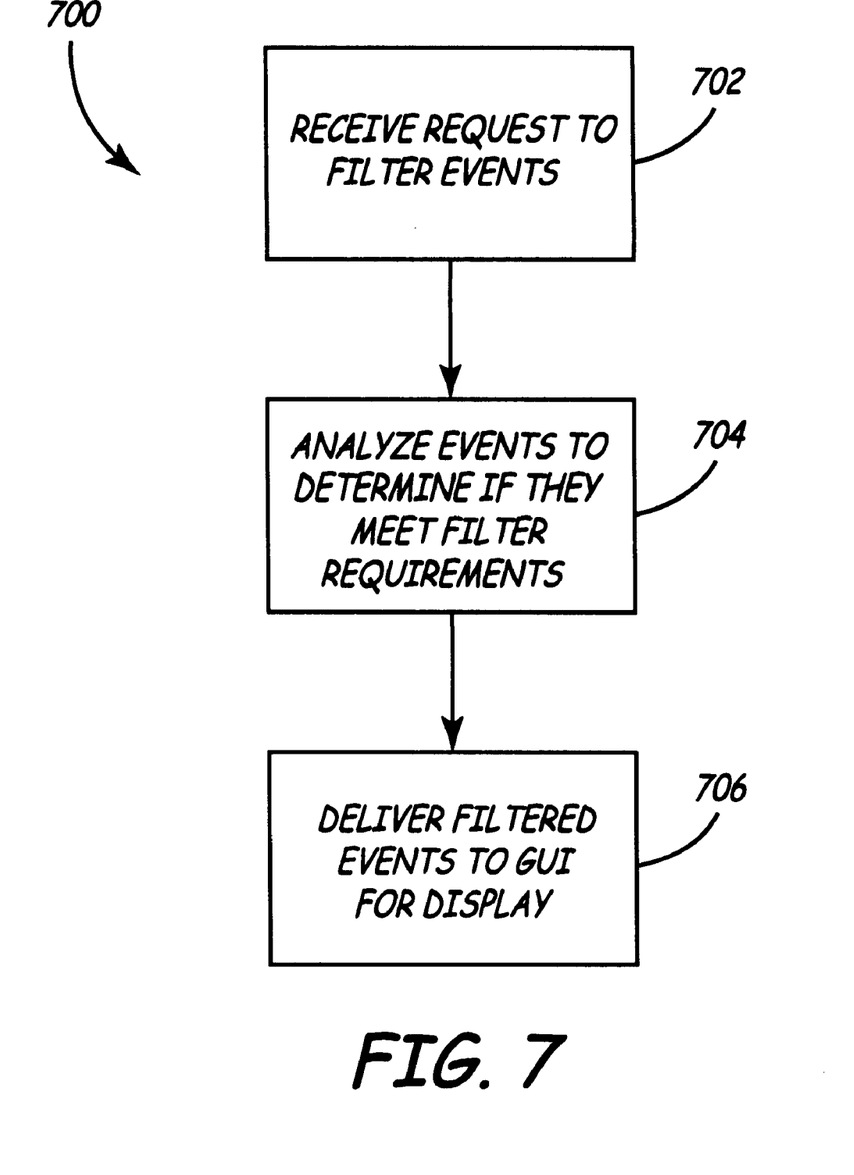
FIG. 7 illustrates one embodiment of a flowchart representation of a software program used to control at least a portion of the graphical user interface of FIGS. 5 and 6.

FIG. 7 illustrates an exemplary embodiment of top level view of a flowchart of a process 700 that may be executed by the processor 10 to effect control of information presented on the display 64 of the processing unit 20. The process 700 begins at block 702 with the software receiving a request to filter the events. That is, the physician/clinician has selected one or more of the types of events identified in the area 514 of the GUI. In block 704, the process 700 analyzes the stored data to determine and identify which events, if any, have characteristics selected by the physician/clinician. In block 706, the process 700 then delivers the identified events to the GUI to be displayed in the window 500.

Figure 8:
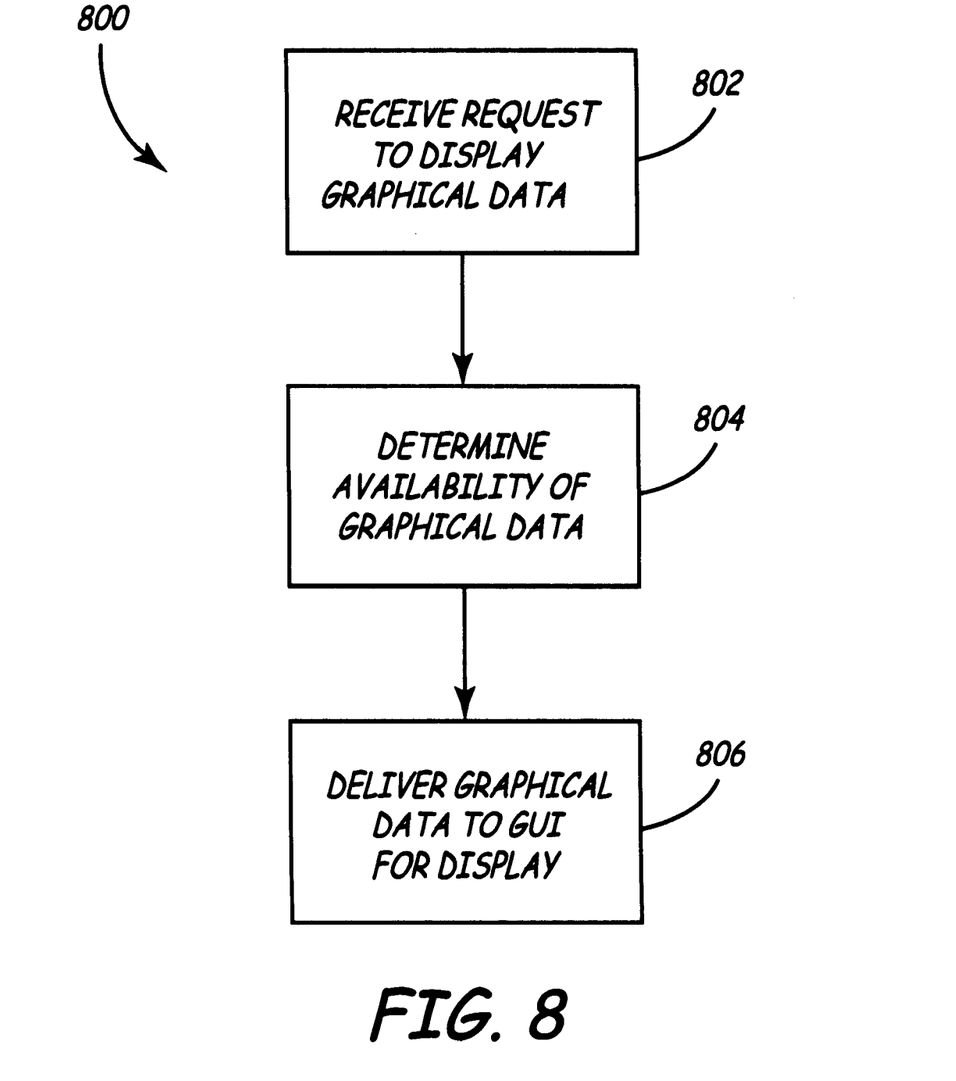
FIG. 8 illustrates one embodiment of a flowchart representation of a software program used to control at least a portion of the graphical user interface of FIGS. 5 and 6.

FIG. 8 illustrates an exemplary embodiment of a top level view of a flowchart of a process 800 that may be executed by the processor 10 to effect control of graphical information presented on the display 64 of the processing unit 20. The process 800 begins at block 802 with the software receiving a request to display graphical data. That is, the physician/clinician has selected the type of graphical information to be displayed in the window 500 using the View portion 512 that includes both text and GUI. In block 804, the process 700 determines if the requested graphical data is present in the memory of the programming unit 20. In the event that the requested data is present, the graphical data is delivered to the GUI, which displays the data in the window 510. It will be appreciated that the data presented in the window 510 may be enlarged or reduced to show portions of the graphical data in greater or less detail, as desired by the physician/clinician. As shown in FIGS. 5 and 6, the GUI possesses buttons 520 that may be selected activated, by for example a pointing device, to selectively enlarge or reduce the view of the graphical data in the window 510.

Figure 9:
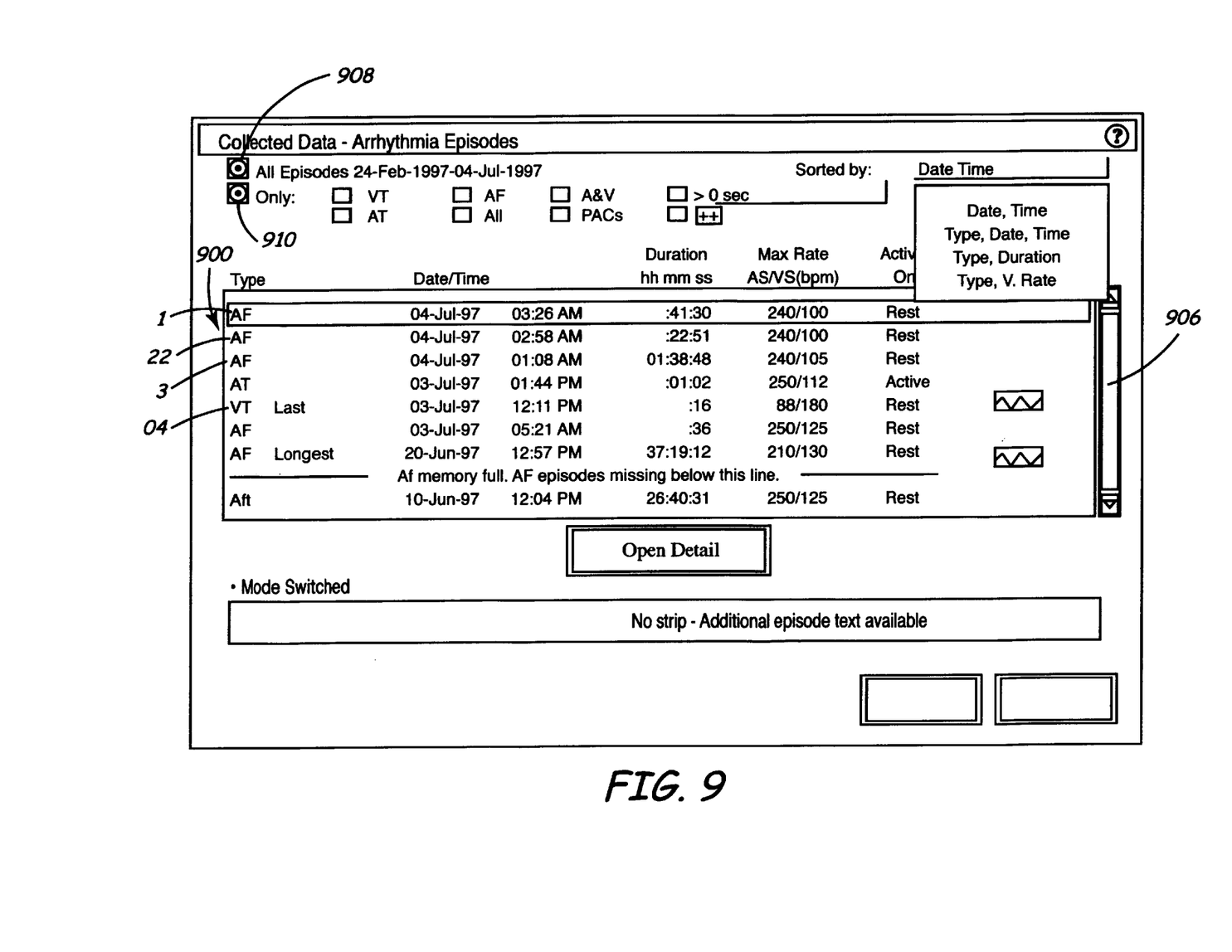
FIG. 9 illustrates an alternative embodiment of a graphical user interface in a first operational state.
Figure 10:
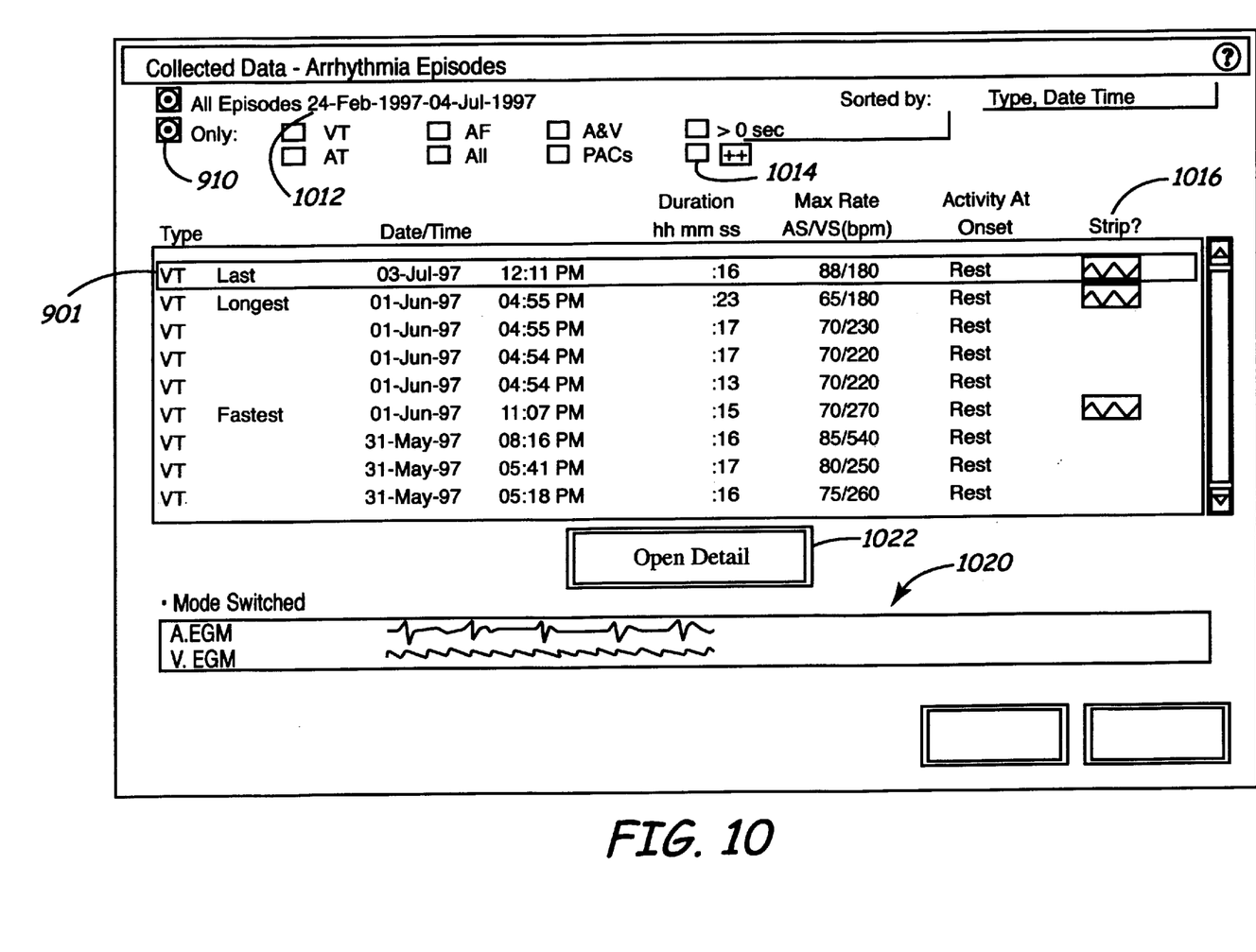
FIG. 10 illustrates an alternative embodiment of a graphical user interface in a second operational state.
Figure 11:
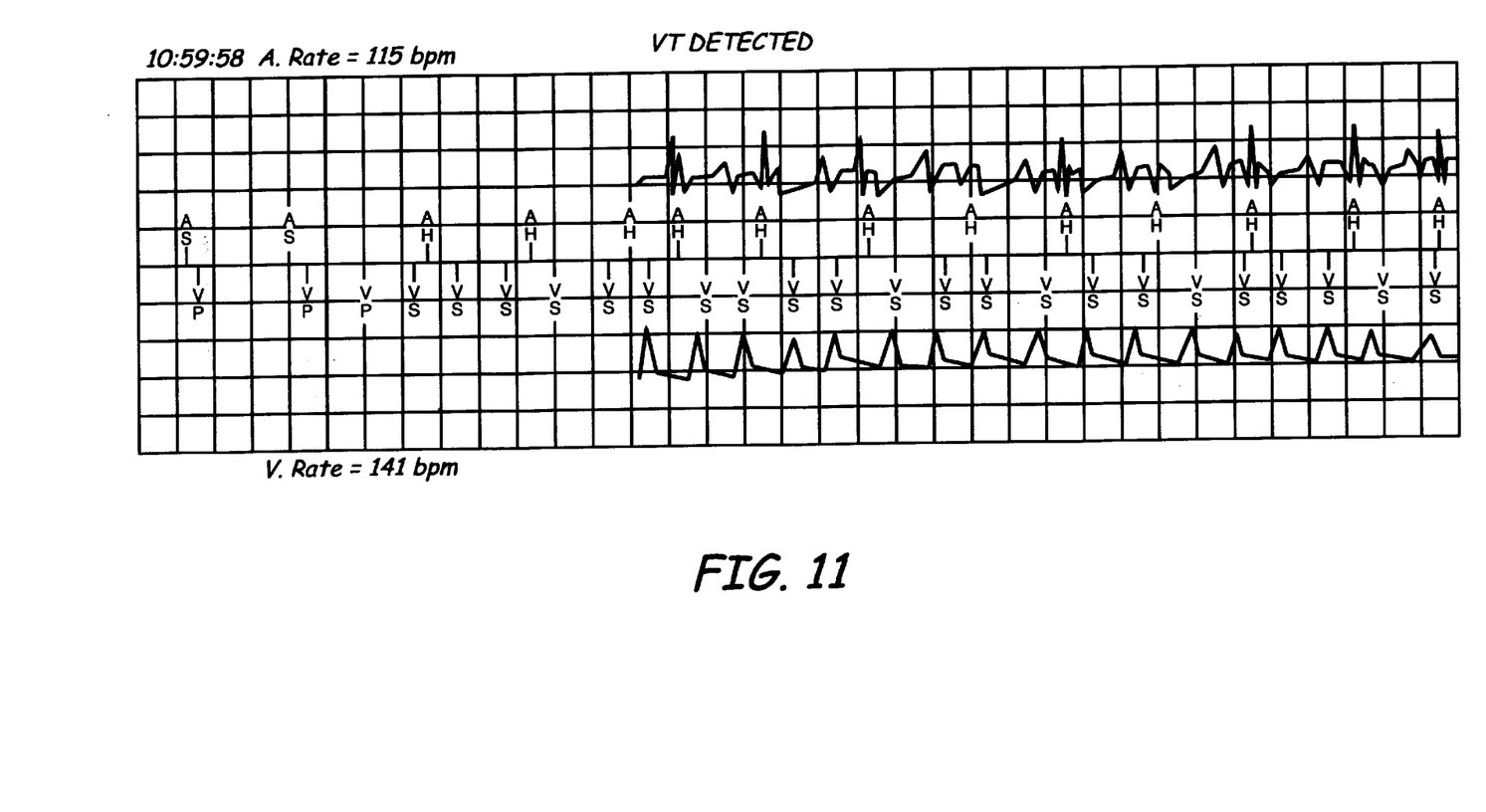
FIG. 11 illustrates an alternative embodiment of a graphical user interface in a third operational state.

Turning now to FIGS. 9–11, an alternative embodiment of the GUI is illustrated. In the embodiment illustrated in FIG. 9, a series of cardiac events are displayed in a window 900, each on a separate line 901, 902, 903, 904. At least a portion of the data associated with each of these events may be set forth in the window 900 on their associated line 901, 902, 903, 904. For example, the line 901 indicates that the illustrated event includes data, such as the type of event, the date, the duration, whether an EGM was recorded, and the like. The listing of events or log contained in the window 900 represent all episodes or events retrieved from the pacemaker 10, although only a portion of these episodes are currently displayed. A slidebar 906 allows the physician/clinician to selectively move the window 900 so as to display additional episodes. All episodes are currently available through the window 900 because the All Episodes radio button 908 has been selected by the physician/clinician.

Where the physician/clinician desires to filter the events to only select types of episodes, he/she may do so by selecting the Only radio button 910, and then picking the types of events that he/she would like to be displayed in the window 900. A single type of event or a plurality of events may be selected to produce the desired log. For example, as shown in FIG. 10, the Only radio button 910 has been selected and the VT box 1012 has been checked. Thus, the window 900 displays only VT type episodes. Further filtering of the log presented in the window 900 may be accomplished by, for example, checking the EGM box 1014. This combination would produce a log that contains only VT episodes in which an EGM has also been recorded (as indicated by the presence of a graphical icon in the Strip field 1016.

The physician/clinician may select one of the events, using the keyboard or other pointing device. For example, the line 901 has been selected in the embodiment illustrated in FIG. 10. Once the desired line has been selected, graphical representations of any data recorded by the pacemaker 10 during the event may be presented in a second window 1020. For example, in the embodiment illustrated in FIG. 10, an EGM associated with the event identified in the line 901 has been displayed in a window 1020. The window 1020 does not display the EGM in detail, but rather, presents a reduced size graph that may or may not be to scale. In this mode of operation, the window 1020 may be referred to as a mini-viewer, as it does not provide all of the details that may be present in the EGM, as recorded by the pacemaker 10. Rather, the purpose of the EGM is to provide a quick, easy-to-read graphical representation to the physician/clinician so that he/she may promptly determine if the data requires or warrants additional study. That is, if the mini-viewer representation of the data looks interesting to the physician/clinician, he/she may request a more detailed view of the graphical data. A more detailed view may be requested by selecting an Open Details button 1022 in the GUI.

One exemplary embodiment of a more detailed view of an EGM may be seen in FIG. 11. The detailed view may include substantially more information than that presented in the mini-viewer 1020, such as horizontal and vertical scaling, including timing and magnitude. Moreover, the detailed view may occupy a substantially larger portion of the display screen 64 so that the details may be more easily presented and viewed for a detailed analysis by the physician/clinician.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. In particular, every range of values (of the form, "from about a to about b," or, equivalently, "from approximately a to b," or, equivalently, "from approximately a–b") disclosed herein is to be understood as referring to the power set (the set of all subsets) of the respective range of values, in the sense of Georg Cantor. Accordingly, the protection sought herein is as set forth in the claims below. Accordingly, the protection sought herein is as set forth in the claims below.

What is claimed:

1. A method for controllably displaying information retrieved from an implantable device, comprising:

displaying data in a first window identifying a plurality of episodes recorded by the implantable device, wherein the data is comprised of a plurality of fields; and displaying data types that are present in the plurality of fields in a second window, wherein at least one of the data types is selected to filter the episodes displayed in the first window and display those episodes having the selected data types.

2. A method, as set forth in claim 1, further comprising displaying in a third window a simplified graphical representation of data associated with a selected one of the episodes.

3. A method, as set forth in claim 2, further comprising selectively displaying in a fourth window a scaled representation of the data presented in the third window.

4. A method, as set forth in claim 2, further comprising selectively displaying in a fourth window a scaled representation of the data presented in the third window, wherein the fourth window replaces at least the third window.

5. A method, as set forth in claim 2, wherein displaying the simplified graphical representation of data associated with the selected one of the episodes further comprises displaying a simplified graphical representation of an electrocardiogram recorded by the implantable device.

6. A method, as set forth in claim 5, further comprising selectively displaying in a fourth window an electrocardiogram recorded by the implantable device.

7. A method, as set forth in claim 1, wherein displaying data types that are present in the plurality of fields in the second window further comprises filtering the episodes displayed in the first window based upon a plurality of selected data types.

8. A method, as set forth in claim 1, wherein displaying data in the first window identifying the plurality of episodes recorded by the implantable device further comprises displaying data in the first window identifying a plurality of cardiac episodes recorded by the implantable device.

9. A method, as set forth in claim 8, wherein displaying data types that are present in the plurality of fields in the second window further comprises displaying types of cardiac events, wherein at least one of the displayed types of cardiac events is selectable to filter the cardiac episodes displayed in the first window and display those cardiac episodes of the selected type in the first window.

10. A method, as set forth in claim 8, wherein displaying data types that are present in the plurality of fields in the second window further comprises displaying types of cardiac events, wherein a plurality of the displayed types of cardiac events is selectable to filter the cardiac episodes displayed in the first window and display those cardiac episodes of the selected types in the first window.

11. A method, as set forth in claim 1, wherein displaying data in the first window identifying the plurality of episodes recorded by the implantable device further comprises displaying data in the first window identifying at least one of a ventricular tachycardia, atrial and ventricular tachycardia, atrial fibrillation, atrial flutter, atrial tachycardia, and premature atrial contraction episodes recorded by the implantable device.

12. A graphical user interface for controllably displaying information retrieved from an implantable device, comprising:

a first window adapted to display data identifying a plurality of episodes recorded by the implantable device, wherein the data is comprised of a plurality of fields; and a second window adapted to display data types that are present in the plurality of fields, wherein at least one of the data types is selected to filter the episodes displayed in the first window and display those episodes having the selected data types.

13. A graphical user interface, as set forth in claim 12, further comprising a third window adapted to display a simplified graphical representation of data associated with a selected one of the episodes.

14. A graphical user interface, as set forth in claim 13, further comprising a fourth window adapted to display a scaled representation of the data presented in the third window.

15. A graphical user interface, as set forth in claim 13, further comprising a fourth window adapted to selectively display a scaled representation of the data presented in the third window, wherein the fourth window replaces at least the third window.

16. A graphical user interface, as set forth in claim 13, wherein the third window is adapted to display a simplified graphical representation of an electrocardiogram recorded by the implantable device.

17. A graphical user interface, as set forth in claim 16, further comprising a fourth window adapted to selectively display an electrocardiogram recorded by the implantable device.

18. A graphical user interface, as set forth in claim 12, wherein the second window is adapted to filter the episodes displayed in the first window based upon a plurality of selected data types.

19. A graphical user interface, as set forth in claim 12, wherein the first window is adapted to display data identifying a plurality of cardiac episodes recorded by the implantable device.

20. A graphical user interface, as set forth in claim 19, wherein the second window is adapted to filter the cardiac episodes displayed in the first window and display those cardiac episodes of the selected type in the first window.

21. A graphical user interface, as set forth in claim 19, wherein the second window is adapted to permit a plurality of the displayed types of cardiac events to be selected to filter the cardiac episodes displayed in the first window and display those cardiac episodes of the selected types in the first window.

22. A graphical user interface, as set forth in claim 1, wherein displaying data in the first window identifying the plurality of episodes recorded by the implantable device further comprises displaying data in the first window identifying at least one of a ventricular tachycardia, atrial and ventricular tachycardia, atrial fibrillation, atrial flutter, atrial tachycardia, and premature atrial contraction episodes recorded by the implantable device.

23. A computer programmed to perform a method for controllably displaying information retrieved from an implantable device, the programmed method comprising:

displaying data in a first window identifying a plurality of episodes recorded by the implantable device, wherein the data is comprised of a plurality of fields; and displaying data types that are present in the plurality of fields in a second window, wherein at least one of the data types is selected to filter the episodes displayed in the first window and display those episodes having the selected data types.

* * * * *